(12) United States Patent
Pellaton et al.

(10) Patent No.: US 7,748,274 B2
(45) Date of Patent: Jul. 6, 2010

(54) DOCUMENT INSPECTION SYSTEM

(75) Inventors: Cyril Pellaton, Colombier (CH);
Ronald Bruce Blair, Flower Mound, TX (US); Jerry Edwards, Irving, TX (US); John Mouser, Plano, TX (US)

(73) Assignee: De La Rue International Limited, Hampshire (GB)

( * ) Notice: Subject to any disclaimer, the term of this patent is extended or adjusted under 35 U.S.C. 154(b) by 103 days.

(21) Appl. No.: 11/989,227

(22) PCT Filed: Aug. 8, 2006

(86) PCT No.: PCT/GB2006/002947

§ 371 (c)(1),
(2), (4) Date: Mar. 7, 2008

(87) PCT Pub. No.: WO2007/017663

PCT Pub. Date: Feb. 15, 2007

(65) Prior Publication Data

US 2009/0260440 A1   Oct. 22, 2009

Related U.S. Application Data

(60) Provisional application No. 60/706,753, filed on Aug. 10, 2005.

(51) Int. Cl.
*G01H 11/00* (2006.01)
(52) U.S. Cl. .............................. 73/649; 73/587; 73/620; 73/625
(58) Field of Classification Search .................. 73/649, 73/580, 587, 618, 620, 624, 625, 628, 635, 73/636
See application file for complete search history.

(56) References Cited

U.S. PATENT DOCUMENTS

| 3,384,234 | A | * | 5/1968 | Elmore | 209/534 |
| 4,446,735 | A | * | 5/1984 | Weilacher | 73/597 |
| 4,548,081 | A | * | 10/1985 | Wolthausen | 73/584 |
| 4,612,807 | A | * | 9/1986 | Wunderer | 73/580 |
| 5,661,243 | A | * | 8/1997 | Bryan et al. | 73/632 |
| 5,691,474 | A | * | 11/1997 | Gerz | 73/580 |
| 5,922,960 | A | * | 7/1999 | Toda | 73/597 |
| 6,407,964 | B1 | * | 6/2002 | Hornung et al. | 367/138 |
| 6,595,060 | B2 | * | 7/2003 | Wunderer et al. | 73/597 |
| 6,763,721 | B2 | * | 7/2004 | Wunderer et al. | 73/602 |
| 7,469,589 | B2 | * | 12/2008 | Pradel | 73/602 |
| 2004/0021850 | A1 | * | 2/2004 | Evans et al. | 356/71 |
| 2008/0276711 | A1 | * | 11/2008 | Nichiforenco et al. | 73/643 |
| 2009/0133502 | A1 | * | 5/2009 | Gret et al. | 73/633 |

FOREIGN PATENT DOCUMENTS

EP    0 740 154 A1    10/1996

* cited by examiner

*Primary Examiner*—Hezron Williams
*Assistant Examiner*—Samir M Shah
(74) *Attorney, Agent, or Firm*—Oliff & Berridge PLC

(57) ABSTRACT

Document inspection system comprising a transport system for transporting documents along a transport path (12) through an inspection station. At least one ultrasonic inspection apparatus at the inspection station, the apparatus including ultrasonic transmitting and receiving transducers (42,44) arranged on opposite sides of the transport path, and a processing system for monitoring ultrasonic signals received by the receiving transducer. An ultrasonic absorbing material (300) is provided around the transducers and facing the transport path for absorbing ultrasound reflected by a document. Document guide apparatus (312,314), having a lower coefficient of friction than the absorbing material, extends partially over the absorbing material (300) so as to prevent documents contacting the absorbing material in use while leaving the absorbing material exposed to the transport path at least adjacent the transducers.

22 Claims, 16 Drawing Sheets

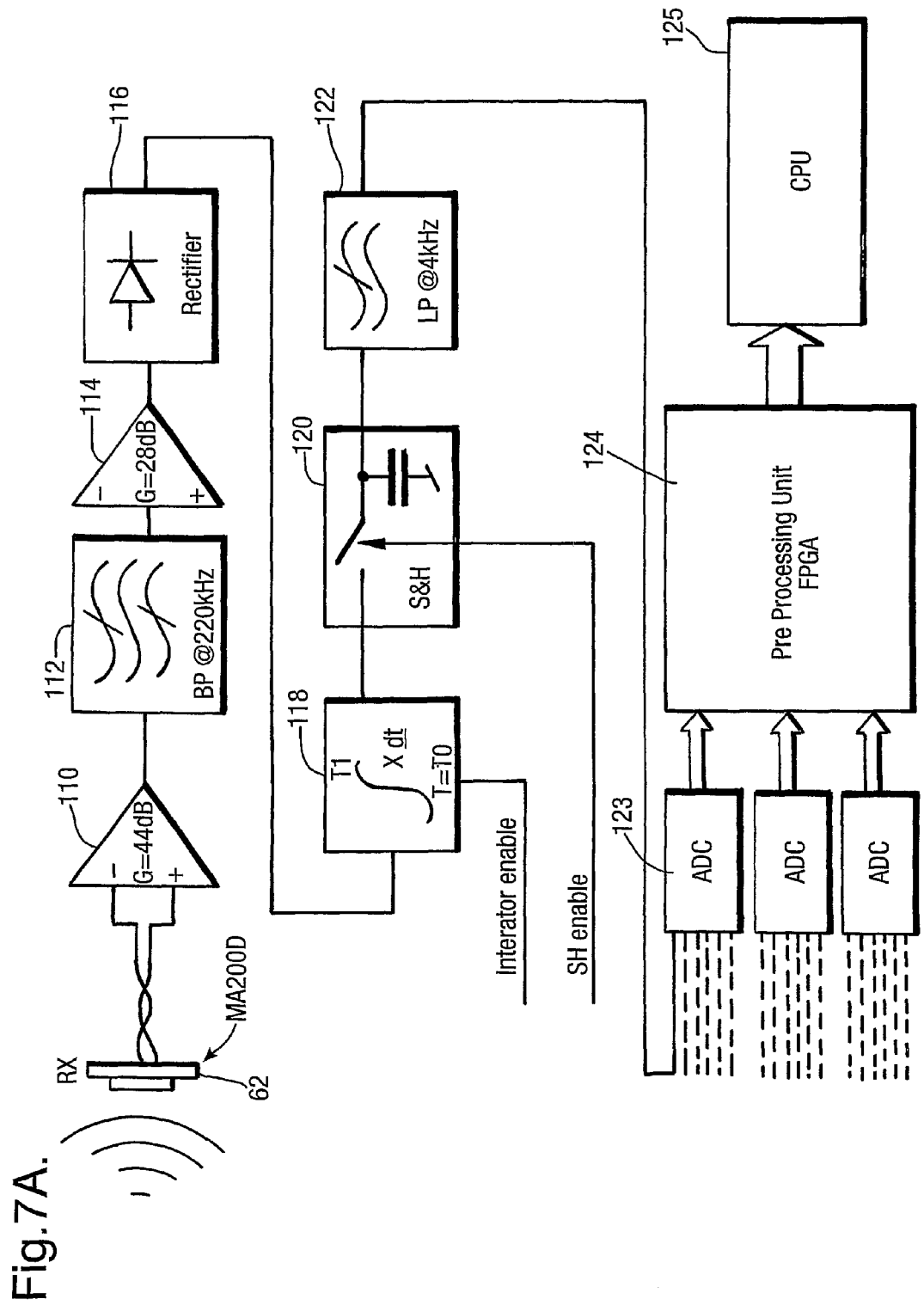

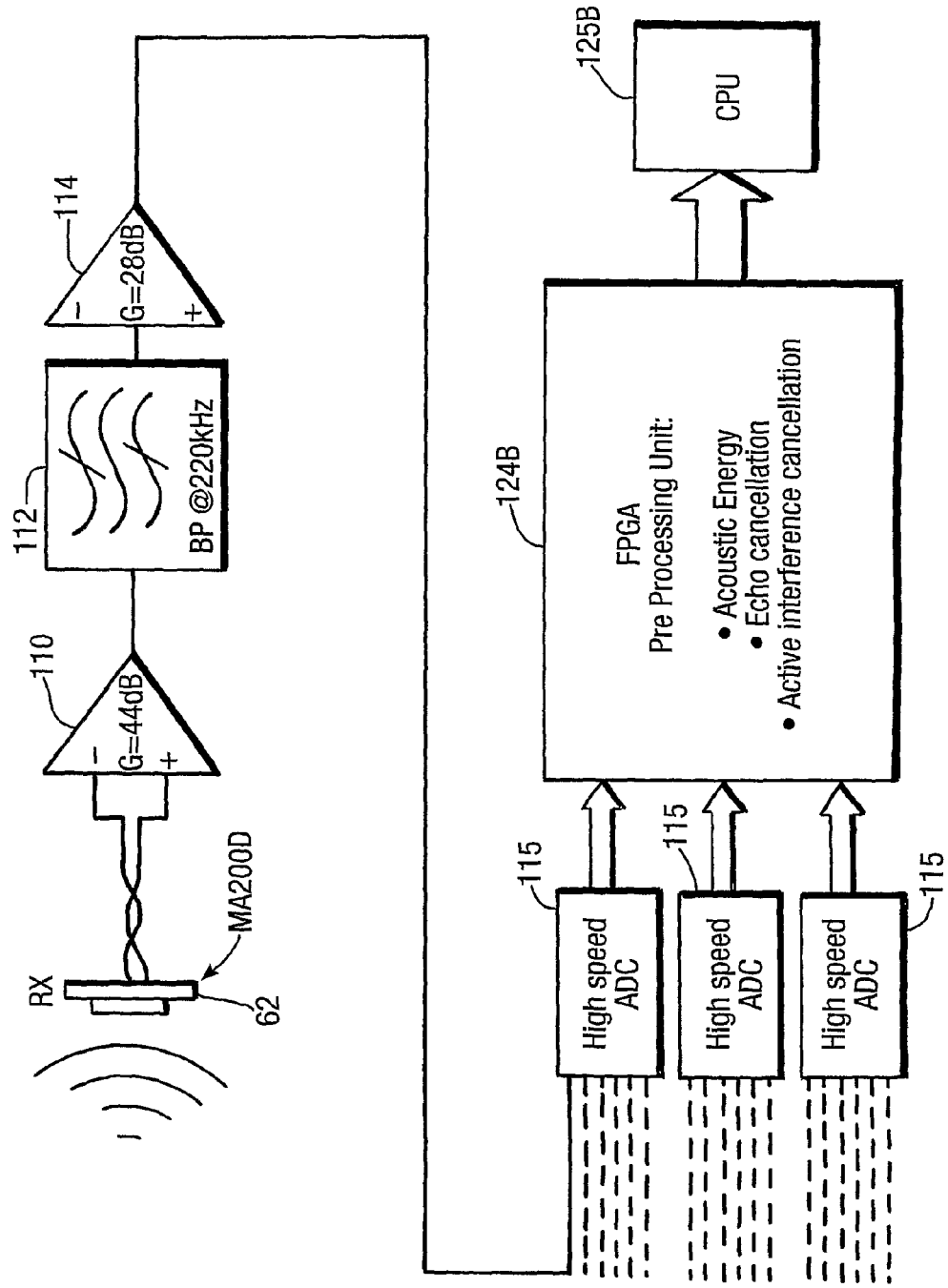

DRE 100 - No tape

DRE 100 - Mate tape

DRE 100 - Crystal tape

CHF 20 - Tape and Micro perforation

EUR 5 - No Tape

EUR 5 - Tape on thread

Burst rate: 233 us, 30°, 2cm

Burst rate: 109 us, 30°, 2cm

Burst rate: 918 us, 30°, 2cm

Burst rate: 123 us, 30°, 2cm

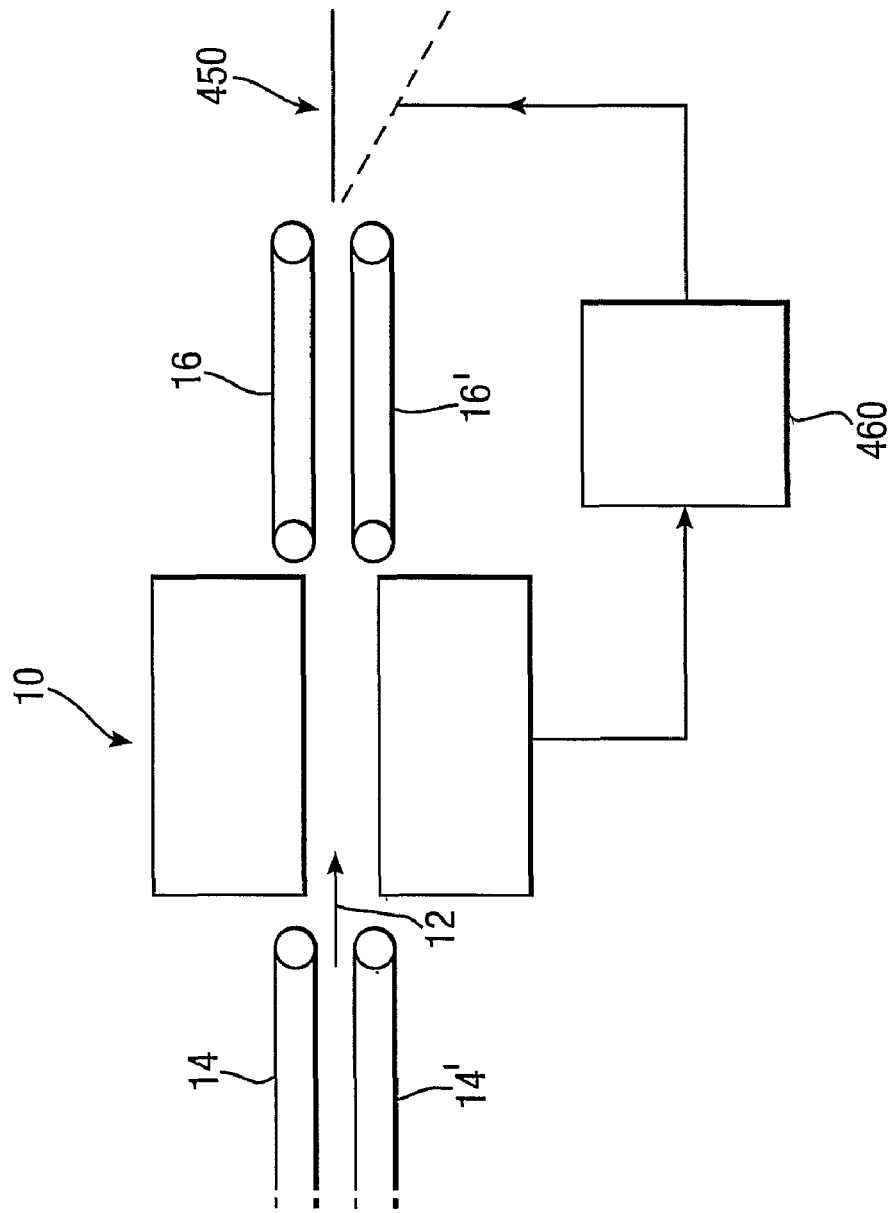

DOCUMENT INSPECTION SYSTEM

The invention relates to a document inspection system of the kind comprising a transport system for transporting documents along a transport path through an inspection station; at least one ultrasonic inspection apparatus at the inspection station, the apparatus including ultrasonic transmitting and receiving transducers arranged on opposite sides of the transport path, and a processing system for monitoring ultrasonic signals received by the receiving transducer.

Apparatus of this kind is used widely for monitoring security documents such as banknotes in order to provide an indication of thickness (as in doubles detection). It may also be used for tape detection (i.e. to detect adhesive tape used to repair a tear in a note), watermark detection and inspection (i.e. detection of the presence or absence of a watermark and its pattern), tear detection (both closed where the tear does not extend to the edge and open where the tear does extend to the edge), corner fold detection and detection of security threads. The principle of operation of these systems is to detect the intensity of ultrasound either transmitted through or reflected by a banknote from which certain information about the banknote can be deduced.

In order to achieve accurate coverage of a banknote, more than one pair of ultrasonic transducers and receivers is usually provided, the transducer pairs being arranged side by side, typically across the banknote transport path. A problem which arises in these situations, particularly where documents are being transported at high speed such as up to 10 m/s (equivalent to 1800 notes/minute), is that any undesirable ultrasound reflections do not have time to dissipate and serve to introduce noise into the received signal.

U.S. Pat. No. 6,407,964 describes one attempt at solving this problem by angling the line of sight between the pair of transducers in the direction of document movement so that any reflected ultrasound is directed away from the receiving transducer. A problem with this arrangement is that in practice further transducer pairs are often provided upstream and/or downstream in the transport direction and there is a risk that the reflected ultrasound will interfere with those transducer pairs.

In accordance with a first aspect of the present invention, a document inspection system of the kind described is characterised by an ultrasonic absorbing material provided around the transducers and facing the transport path for absorbing ultrasound reflected by a document; and document guide apparatus, having a lower coefficient of friction than the absorbing material, extending partially over the absorbing material so as to prevent documents contacting the absorbing material in use while leaving the absorbing material exposed to the transport path at least adjacent the transducers.

In this aspect of the invention, we introduce an ultrasound absorbing material around the transducers so that any reflected ultrasound is absorbed by that material and not reflected. However, we have recognized that typical ultrasonic absorbing material could significantly inhibit passage of documents along the transport path since it is important for the transducers and hence the ultrasonic absorbing material to be close to the transport path. If a document passing along the transport path is not kept perfectly flat then there is a risk that part of the document will contact the ultrasonic absorbing material which typically has a relatively high coefficient of friction and jamming or at least retardation of document movement can occur. We have therefore proposed that an additional document guide apparatus is provided extending partially over the absorbing material so as to prevent documents contacting the absorbing material. Of course, the document guide apparatus must still allow a clear line of sight between the transducer pair although, in some cases, it is possible for that line of sight to be partially obscured. For example, if the ultrasound had sufficient intensity this might be acceptable.

In this aspect of the invention, preferably the line of sight between the transducers extends substantially orthogonal to the transport path. The line of sight could be at a non-orthogonal angle but is preferably orthogonal to minimise the chance of ultrasound being reflected along the transport path.

In one example, the document guide apparatus includes a document guide having one or more rails. These may extend parallel with each other and parallel with the transport path or at a non-orthogonal angle to the transport path. Alternatively, the document guide apparatus can comprise a document guide comprising a plate with respective apertures associated with the or each transducer to enable ultrasound to travel through the plate. This reduces the risk of contact between a document and the ultrasonic absorbing material than in the case of rails.

Preferably, however, the document guide apparatus includes a document guide having both a plate and one or more rails. This combination could be machined from a single metal substrate to minimize cost and for ease of assembly.

Typically, the document guide apparatus comprises a pair of said document guides on either side of the transport path, one associated with the transmitting transducer(s) and the other associated with the receiving transducer(s).

The absorbing material may be made of a polyurethane foam, typically of low density.

As explained above, the first aspect of the invention provides a way of utilizing an ultrasonic absorbing material without impeding the movement of documents and allowing high speed operation.

A possible drawback of that approach is the requirement for ultrasonic absorbing material. Therefore, we provide in accordance with a second aspect of the present invention, a document inspection system of the kind described characterised in that the pair of transducers define a line of sight between them which extends i) in a plane orthogonal to the transport path, and ii) at a non-orthogonal angle to the transport path, the angle being chosen so that ultrasound reflected by a document on the transport path will be reflected into the housing where it will dissipate without being received by a transducer.

In this aspect, firstly the line of sight between the pair of transducers extends at a non-orthogonal angle to the transport path in a plane orthogonal to the transport path so that ultrasound is reflected to either side of the transport path, and secondly the arrangement is such that the reflected ultrasound is reflected into the housing where it will dissipate. This will require careful placement of the transducer pairs depending upon the construction of the housing so that ultrasound which undergoes a first reflection from a document is directed into the body of the housing where it can undergo further reflections and dissipate without being received by a receiving transducer. Typically, the line of sight extends at 30° or 45° to the transport path.

In both aspects, the system may further comprise a plurality of said ultrasound inspection apparatus arranged in a linear array, the line extending transverse, preferably orthogonal, to the transport path. This arrangement then allows the full width, transverse to the transport direction, of a document to be inspected.

In order to increase the rate at which information can be obtained from a document, preferably the system further comprises more than one of said linear arrays, the arrays being arranged side by side in a direction along the transport path.

Due to the physical size of each transducer, within one array, there will be certain regions between adjacent transducers which correspond to unmonitored regions of a document. To overcome this, the transducers of one array are preferably offset in the array direction with respect to the transducers of an adjacent array.

Some examples of document inspection systems according to the system will now be described with reference to the accompanying drawings, in which:—

FIGS. 7A and 7B are block circuit diagrams of receiving transducer processing circuits;

Figure 1:
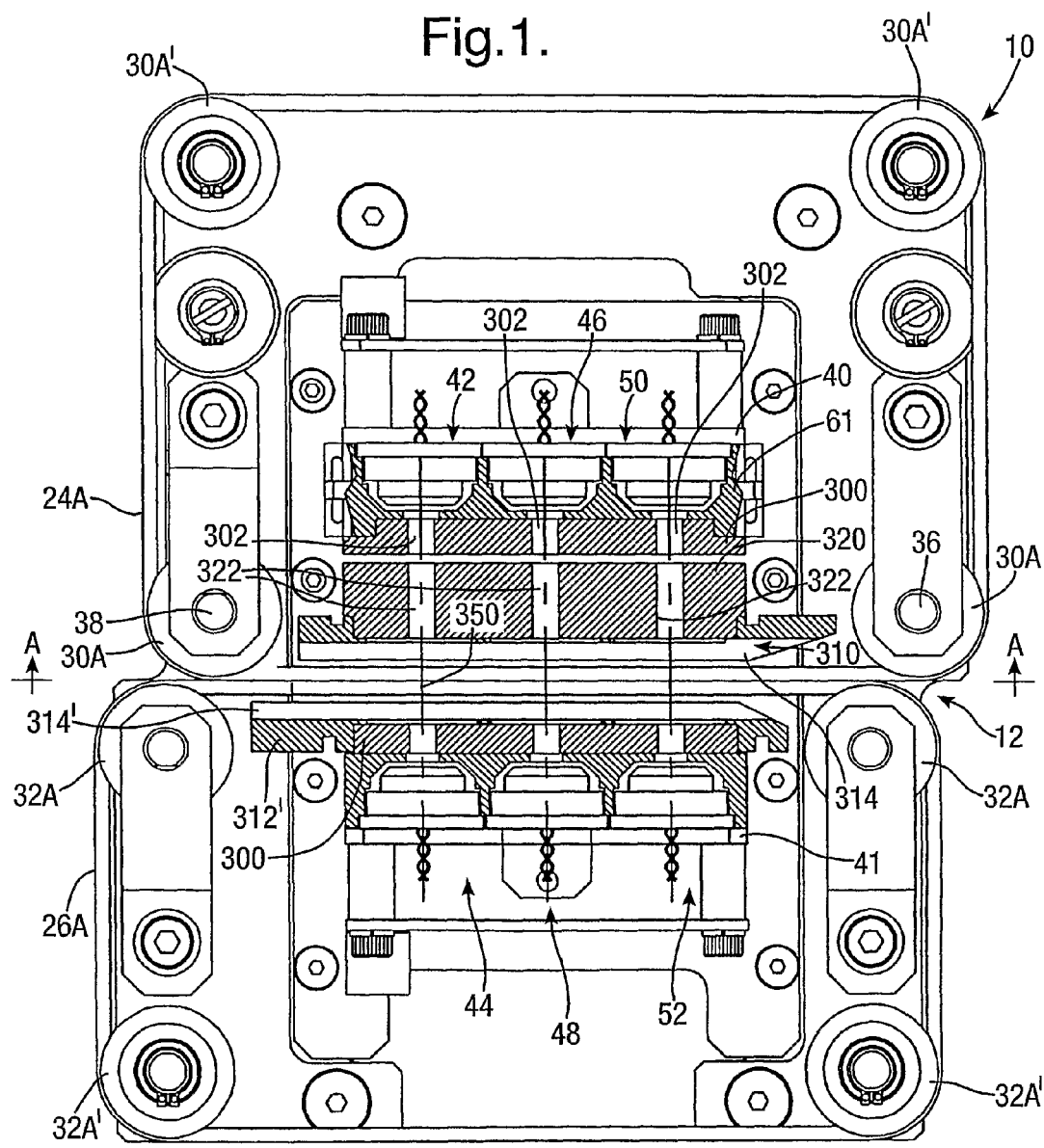
FIG. 1 is a side elevation, partly in section, of a first example of the detector.

The document inspection system shown in FIGS. 1-4 is indicated at 10 and is located adjacent part of a banknote transport path 12 of a banknote sorter (described in more detail below in connection with FIG. 31) in which banknotes pass from right to left in the drawing.

Figure 2:
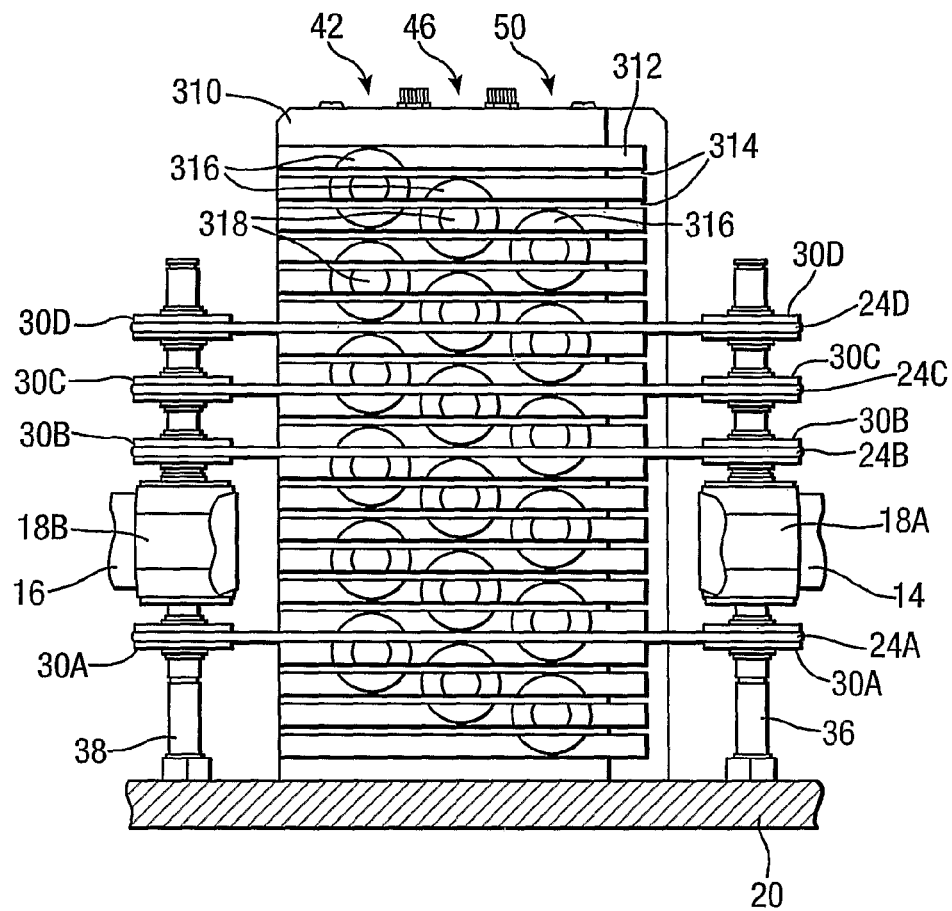
FIG. 2 is a view on the line A-A in FIG. 1.

The part of the transport path 12 adjacent the detector 10 is defined by upper and lower pairs of conveyor belts 14, 16, the upper belts 14, 16 of each pair being visible in FIG. 2. The belts 14, 16 extend generally along the centre of a banknote as it is being transported. Each upper belt 14, 16 is entrained around rollers 18A, 18B mounted to a base plate 20 via shafts 36,38, while the lower belt 16 is entrained similar rollers also mounted to the base plate 20 via further respective shafts.

In order that banknotes are conveyed through the detector 10, a set of four, upper and lower aligned pairs of thin laterally spaced O-rings 24A-24D; 26A-26D (26B-26D not shown) are provided extending through the detector 10 and entrained about respective rollers 30A-30D; 32A-32D. The two lower rollers of each set 30A,30B,30C, 30D are respectively mounted non-rotatably on the shafts 36,38 to which the rollers 18 are also mounted, the shafts being rotatably journalled in the base plate 20. The O-rings also extend around respective rollers 30A'-30D'; 32A'-32D'. The O-rings are driven by belt 14 causing rotation of shaft 36 via roller 18A which is fixed to shaft 36.

A pair of sensor mounting plates 40,41 are secured to the roller mounting plate or base plate 20 and three pairs of upper and lower sensor arrays 42,44; 46,48; and 50,52 respectively are mounted to the mounting plates 40,41.

Each sensor array 42-52 has a similar construction but with the sensors located slightly differently and so the array 42,44 will be described in detail.

Figure 3:
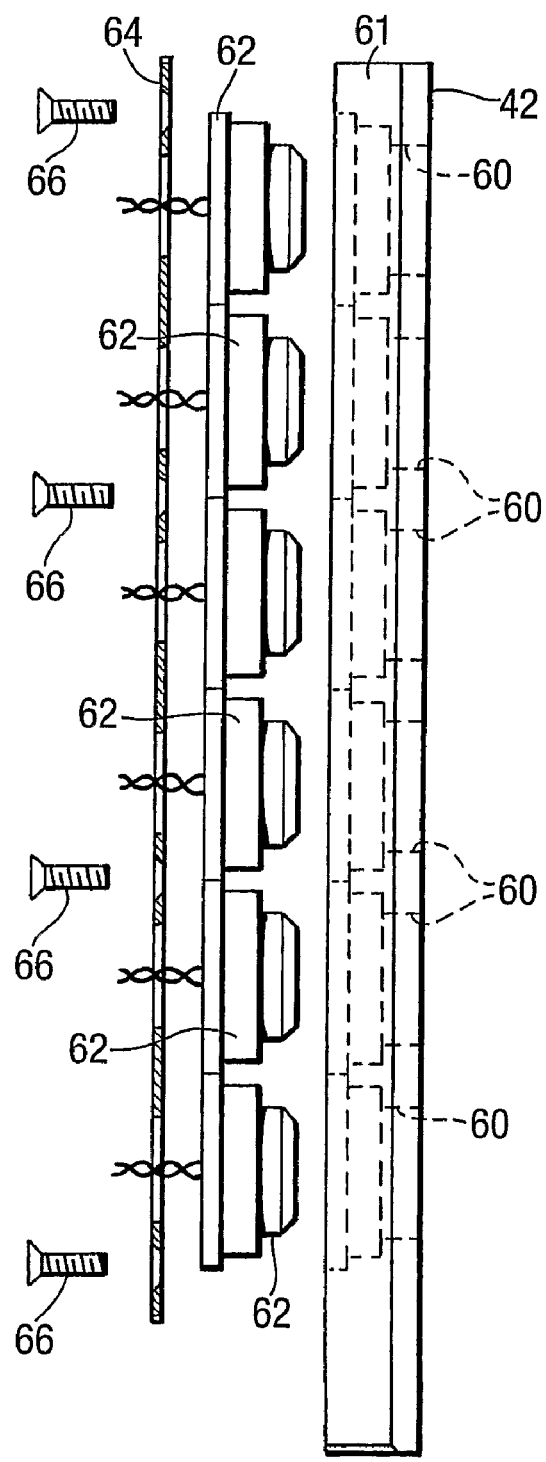
FIG. 3 is an exploded view of one of the sensor arrays shown in FIG. 1.

As can be seen in FIG. 3, the sensor array 42 has six sensor locations 60 arranged in a line adjacent one another in a housing member 61. As can be seen in FIG. 1, the housing member 61 also provides locations for the other arrays of transducers 46,50. Into each location is mounted a respective ultrasonic transducer 62, the transducers being held in place by a rear cover 64 secured by screws 66.

Each transducer 62 is a high frequency ultrasonic transducer, for example of the type MA200D made by Murata Manufacturing Co. Ltd. Table 1 below sets out the primary properties of the transducers 62.

TABLE 1

| Items | Specification | Note |
|---|---|---|
| Nominal Freq. | 220 ± 20 kHz | — |
| Overall Sensitivity | 1.0 to 2.5 Vp-p | Drive signal: Burst with 10 Vp-p |
| | | Drive frequency: 220 kHz |
| | | Drive wave number: 5 cycles |
| | | Drive cycle: 220 Hz |
| | | Amplification rate: 1000 times |
| | | Distance between the sensor and aluminum reflecting plate: 150 mm |
| | | Surrounding condition: open space |
| | | Measurement point: Vp-p |
| Directivity | 20 deg. max. | At −6 dB |
| Capacitance | 2300 pF ± 20% | At 1 kHz |
| Max. continuous driving voltage | 12 Vp-p | The rectangle wave |
| Operating Temperature Range | −20 to 70° C. | — |
| Storage Temperature Range | −30 to 70° C. | — |
| Insulation Resistance | 100 Mohm min. | At 100 Vdc |

In the preferred example, the transducers emit at wavelengths of about 1.5 mm corresponding to a frequency of about 220 kHz. However, higher frequencies, potentially as high as 10 MHz, could be used.

The transducers 62 of the arrays 42,46,50, in this example, transmit ultrasonic signals while the transducers in the arrays 44,48,52 receive ultrasound originating with the respective transmitting transducers. However, in other examples, in order to reduce the risk of interference, the transducers of the arrays 46,48 could be inverted so that ultrasound is transmitted in the opposite direction to the other two array sets.

Furthermore, in some cases, a single channel i.e. a single transmitting transducer and a single corresponding receiving transducer, could be used in the detector 10 rather than several arrays. However, it is beneficial to use arrays of sensors in order to achieve better coverage of the documents and detect small tears and openings which would otherwise be missed by a single channel.

Adhered to the housing member 61 is a layer of acoustic foam 300 having apertures 302 aligned with the centre of each transmitting transducer 42,46,50 of each array.

A separate transmitting transducer baffle 310 is provided machined out of aluminium and defining a guide plate portion 312 and a set of parallel rails 314 extending parallel with the transport direction. The plate portion 312 has a set of apertures 316 aligned with the apertures 302 while the rails 314 extend on either side of the most sensitive sections 318 of the transducer transmitting sections. In this way, ultrasound transmitted by the transducers is not significantly inhibited by the rails 314 or the plate 312.

A further layer of acoustic foam 320 is adhered to the upper surface of the plate 312 and has apertures 322 aligned with the apertures 302.

The manner in which the receiving transducers 44,48,52 of the three arrays are mounted is similar to that shown in FIG. 3 and a guide plate 312', rails 314' and acoustic foam 300 is provided similar to that for the transmitting transducers. However, it is not necessary in this case to provide an additional layer of foam corresponding to the foam 320.

As can be seen in FIG. 1, a line of sight extends between each transducer pair 42,44; 46,48 etc. as indicated at 350. This line of sight extends orthogonally to the transport path in both a plane extending in the transport direction as shown in FIG. 1 and in a plane orthogonal to that transport direction.

This means that, in use, any ultrasound reflected by a banknote within the detector system 10 will reflect orthogonally back towards the transducer although, due to movement of the note, this direction will be slightly offset from the orthogonal direction. As a consequence, some of the reflected ultrasound may be absorbed by the acoustic foam. Alternatively, the transducer array may be arranged at an angle to the note transport, e.g. 30°. In this case most of the reflected energy will be absorbed by the acoustic foam.

The rails 314 and plate portion 312 prevent the notes contacting the acoustic foam.

As can be seen in FIG. 2, the three arrays of transducers are laterally offset from one another transverse to the transport direction so that all regions of a banknote can be inspected.

Figure 4:
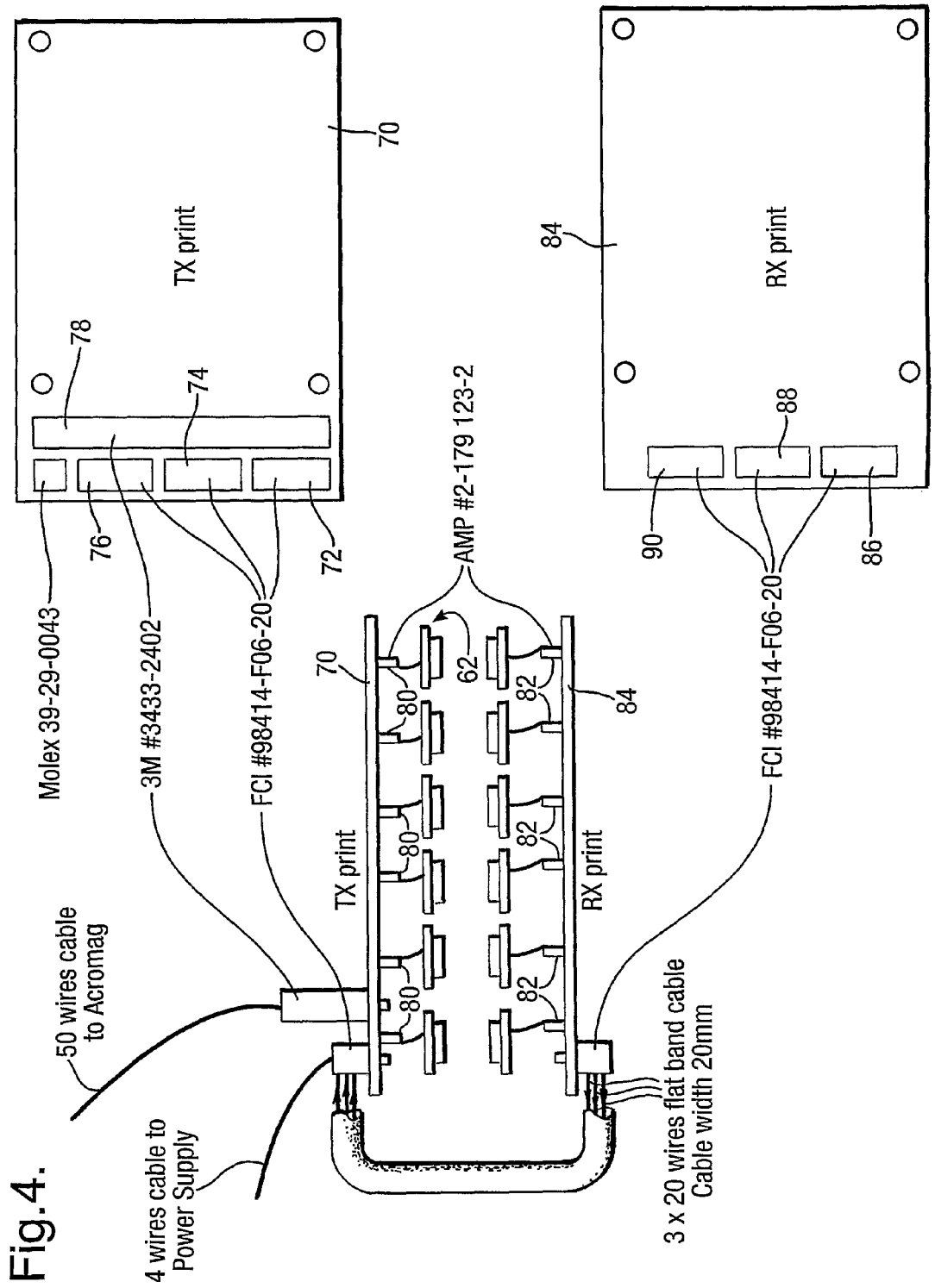
FIG. 4 illustrates schematically the arrangement of transducers and circuit boards.

FIG. 4 shows the circuits for producing, transmitting, receiving and processing of the ultrasonic signals. The transmitting transducers 62 are connected 80 to the transmitting board 70 which houses also the connector 78 for the finished processed digital data to be passed on for further processing. The transmitting circuit 70 is connected by components 72,74,76 and 86,88,90 to the receiving circuit 84 where the receiving transducer elements 82 are also connected. The cables between connectors 72-76,86-90 are used to transmit the following signals:

Power supply
Timing signal for the integrator
Timing signal for the sample-and-hold circuit
Signal from the digitally converted, filtered, sample-and-hold circuit In the example shown in FIGS. 1 to 4, the transducers are arranged in a close-packed fashion as can be seen more clearly in FIG. 2. As already mentioned, a single transducer pair could be used (one channel) or alternatively a single line of channels as defined, for example, by arrays 42,44 could be used. The problem with a single line of channels is, in the case of the MA200D transducer, that the covered area to detect tape, tear or cut is just about 6 mm in diameter. Orthogonal to the transport direction we thus have between each transducer a blind area where we do not detect thread, tears . . . of about 12 mm. Through the arrangement of several relative to each other lateral displaced transducer arrays staggered in transport direction as shown in FIG. 2 a complete coverage of the investigated sheet can be acquired.

For better total performance of the sensor just the transmitting transducer rows could be powered between which a note is located (tracking of note).

Transmitting Transducer Signal Generator

Figure 5:
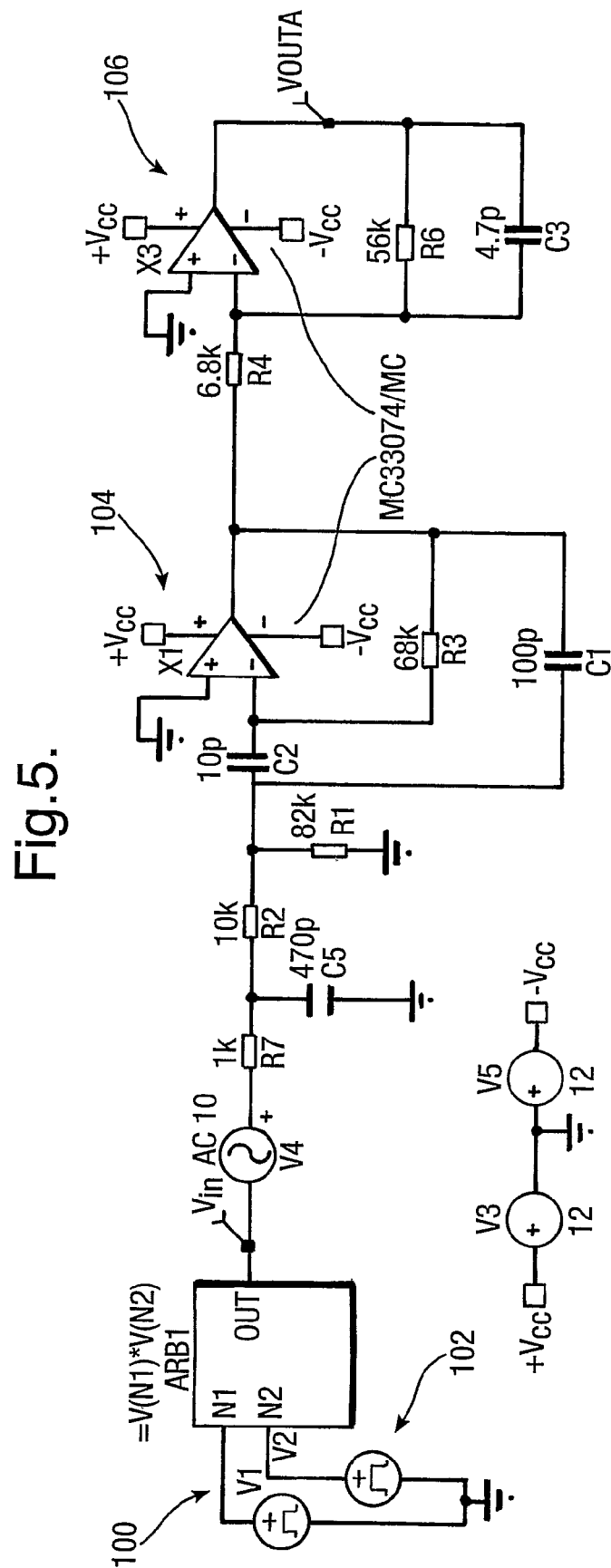
FIG. 5 is a circuit diagram of the transmitter signal generator circuit.

Provided on the PCB 70 for each transmitting transducer 62 is a transmission signal generating circuit 100 (FIG. 5). The circuit comprises a digital pulse signal generator 102 which generates a 5 volt square wave pulse of the required frequency (220 kHz) which is supplied to a filter and amplifier 104,106 which generates a 20 volt sine wave output signal. The timing of operation of the circuits 104,106 is shown in more detail in FIG. 6 (upper trace).

Receiving Transducer Processing Circuit

Each receiving transducer 62 in the arrays 44,48,52 is coupled with its own processing circuit located on the circuit board 84. This circuit is shown in FIG. 7A.

The signals from the receiving transducer 62, which are in the form of a differential output, are fed to a high gain amplifier 110 which, in the example, is an INA103 from Burr Brown having a high bandwidth of 100 kHz at G=1000 and low noise. The differential output from this amplifier is fed to a bandpass filter 112 which has the following characteristics:

| | |
|---|---|
| Bessel bandpass filter | |
| 4 poles | |
| Centre frequency: | 215 KHz |
| 3 dB bandwidth: | 50 KHz |
| Gain | 28 dB |
| Implementation: | 2 stages of Multiple Feedback (MFB) Second order Bandpass |
| Op Amp: | OP162 |

Figure 29:
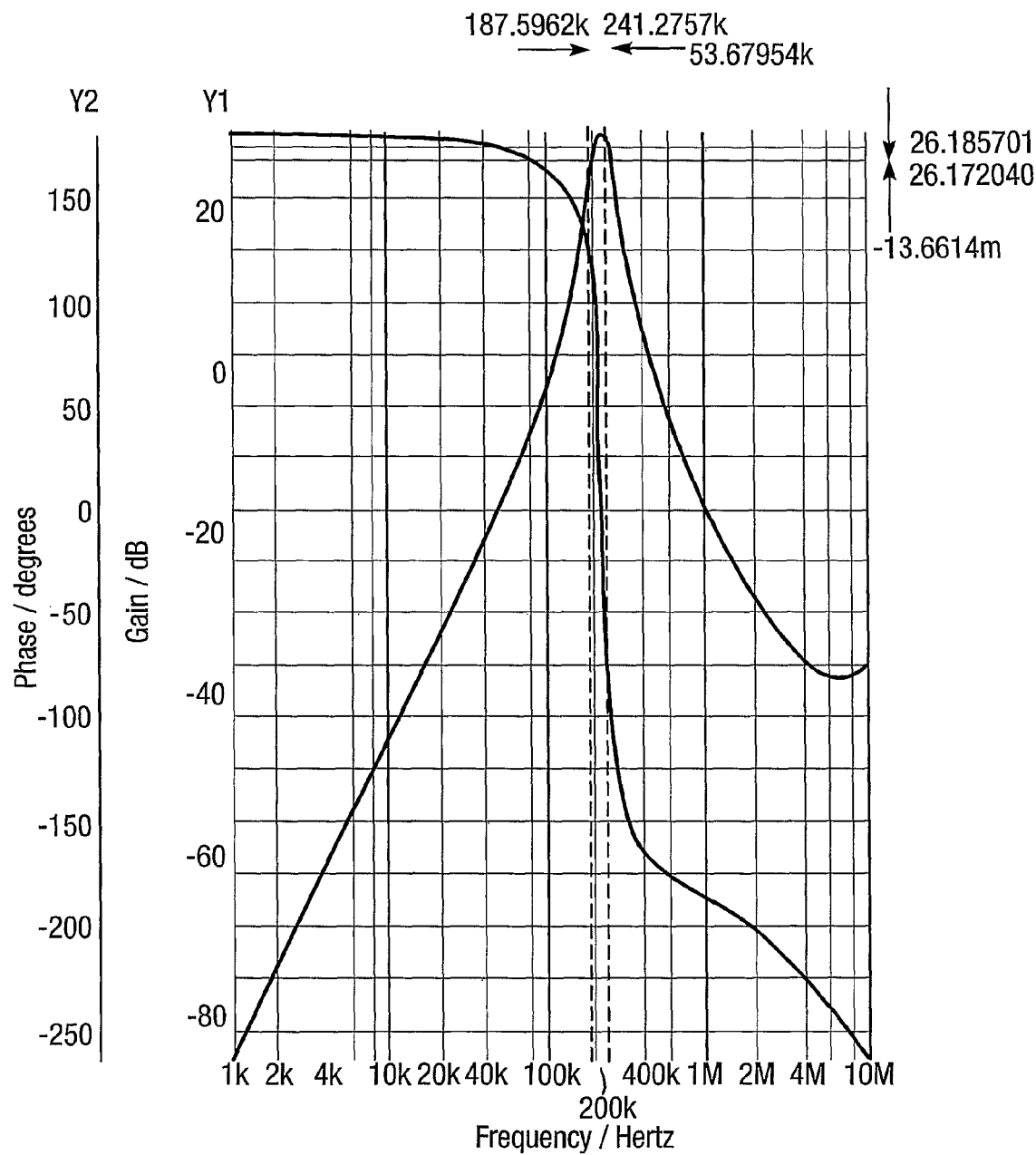
FIG. 29 shows the frequency response of the bandpass filter of the receiver circuit of FIG. 7.

The frequency response of the filter 112 is shown in FIG. 29.

The filtered signal is then further amplified by an amplifier 114 and fed to a rectifier 116.

Figure 6:
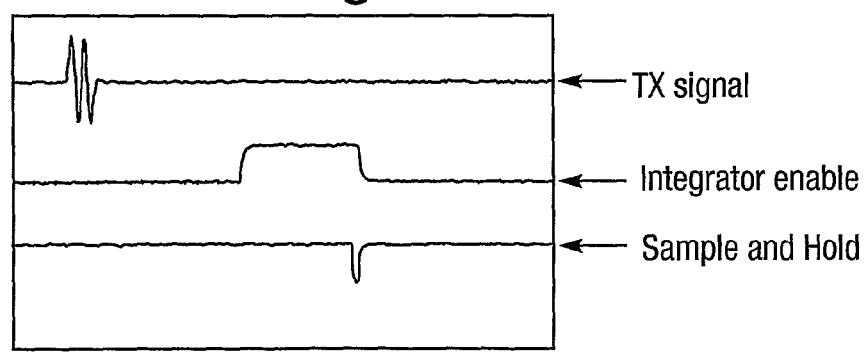
FIG. 6 illustrates the timing sequence of the circuit shown in FIG. 5.

The output of the rectifier is fed to an integrator 118 and the integrated signal is sampled by a sample and hold circuit 120 (operation of the integrator circuit and sample and hold circuit being controlled by respective signals from a programmable logic circuit (not shown)). The final, sampled signal is then passed through a low pass filter 122. FIG. 6 illustrates an example of the timing of operation of the integrator 118 and sample and hold circuit 120.

Each sampled signal is then digitized 123 and fed with digitized signals from other sensors to a preprocessing unit 124 whose output is fed to a CPU 125.

A simpler circuit is shown in FIG. 7B where the components 116-122 have been replaced with high speed Digital-to-Analogue converters and an FPGA and CPU with greater functionality. This circuit, FIG. 7B, uses the same initial amplification and band-pass filter stages 110,112 and 114, but then uses high speed, but low resolution, Analogue-to-Digital converters 115 to convert the analogue signals to digital data. The rectification 116, integration 118, sample-and-hold 120 and low-pass filtering 122 of FIG. 7A is then carried out in a pre-processing FPGA 124B or in a CPU 125B. This is advantageous because costly analogue circuitry is eliminated, the same analogue "front-end" electronics design can be used for other, different, sensors and flexibility is gained by replacing analogue fixed wired electronics with digital configurable logic. These advantages can outweigh the disadvantage of needing a more costly high speed Analogue-to-Digital converter. In the improved design, FIG. 7B, the data is obtained in the high frequency domain which then allows active echo cancellation. Also, a sub-optimal low cost, mechanical set-up, which may create additional echoes ad interference, can be improved by sophisticated digital signal processing.

Figure 8:
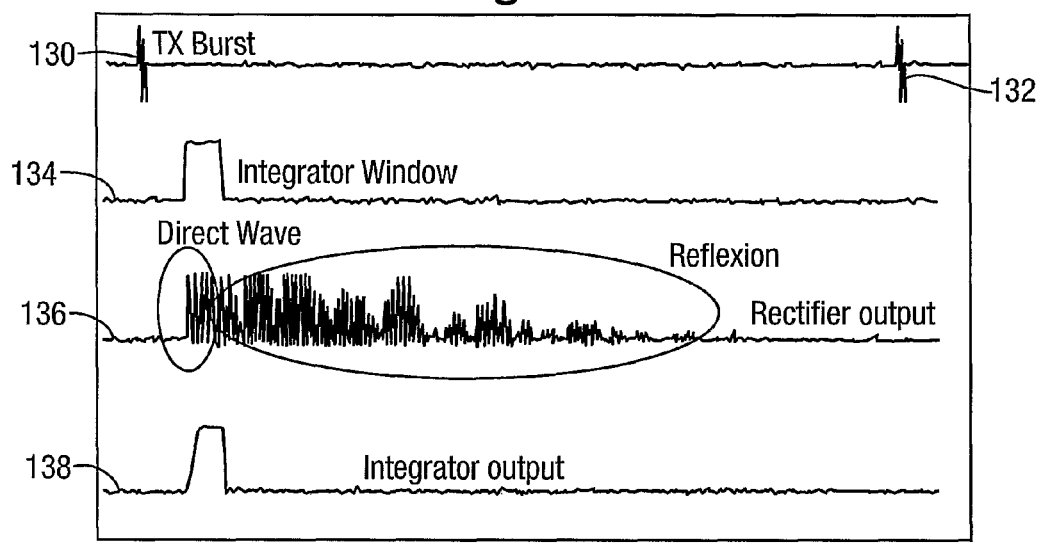
FIGS. 8 and 9 illustrate graphically the transmission and reception of ultrasound signals for a single channel when a document is not present and is present respectively and without acoustic foam.
Figure 9:
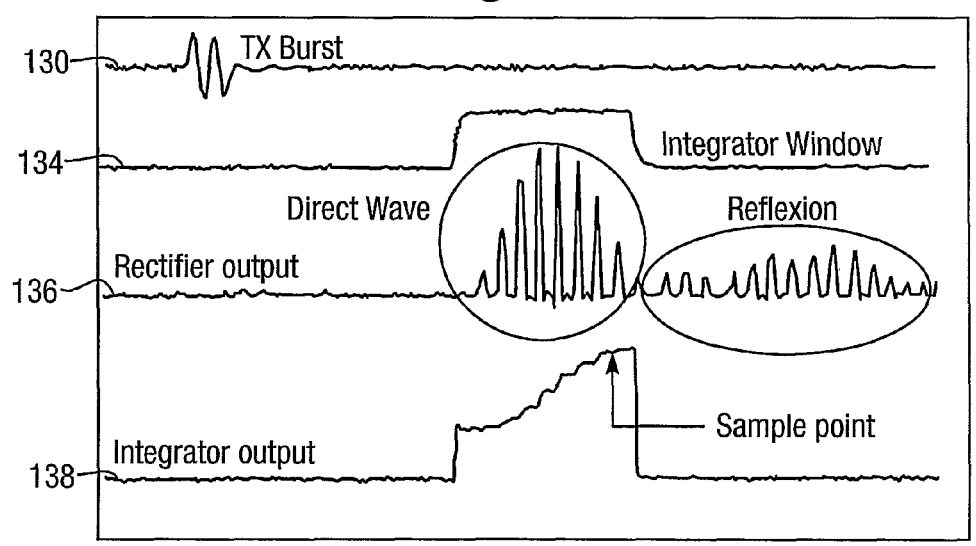

The operation of the receiving circuits shown in FIG. 7 when obtaining information about a single sample point using a single channel is illustrated in FIGS. 8 and 9. In this example, no acoustic foam was used in order to demonstrate the effect of reflections.

FIG. 8 illustrates the situation where there is no document between the transmitting and receiving transducers 62 while FIG. 9, which is on a larger scale, illustrates the signal processing when a document is present.

In this example, the time between commencement of successive bursts of ultrasound from the transmitting transducers is about 900 microseconds.

As can be seen in FIG. 8, bursts of ultrasound are transmitted at points 130,132. Following the transmission of the burst 130, there is a small wait time of 60 μs following which the integrator enable signal 134 is generated to enable the integrator 118. While the integrator is enabled, ultrasound which has traveled directly from the transmitting transducer to the receiving transducer is received by the receiving transducer, the rectified signal being shown at 136, following which the integrator enable signal 134 is terminated so that subsequent ultrasound received by the receiving transducer due to reflections is not processed. The output from the integrator 118 is shown at 138. It will be noted in FIG. 8 that there is a long decay time for all reflections to die away, the next burst 132 occurring only after attenuation of all reflections.

FIG. 9 illustrates the signals obtained and generated when a document is present between the transducers. The traces 130,134 are the same as before and it will be noted that the rectifier output 136 is significantly attenuated relative to the output when no document is present. This is due to absorption by the document. Trace 138 illustrates the effect of integrating the received signal during the integrator window.

Channel Operation

The theory behind the invention will now be described with reference to the structural configuration and operation of a single channel.

Figure 10:
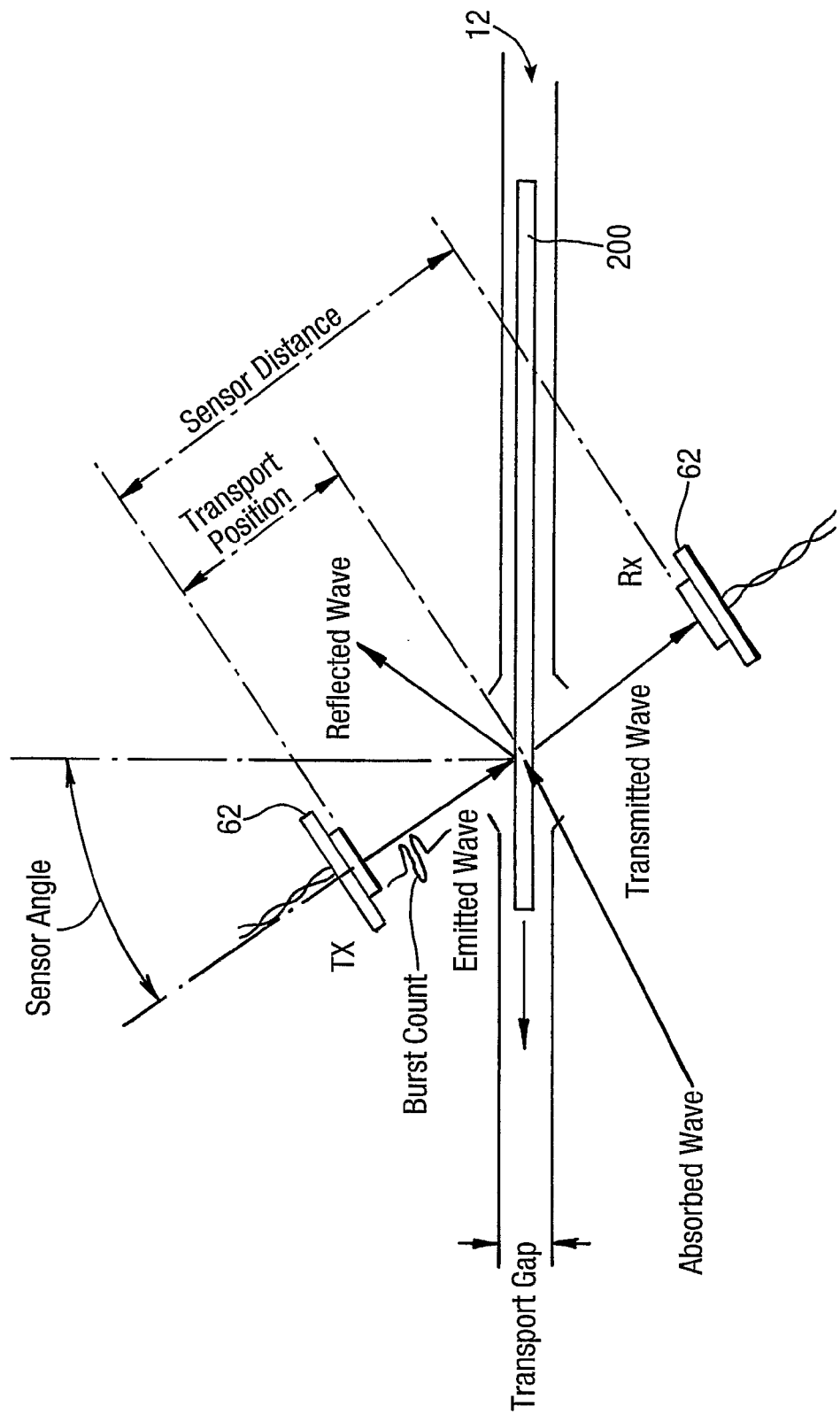
FIG. 10 is a schematic view of a single channel illustrating critical parameters.

FIG. 10 illustrates the configuration of a single channel and the parameters which affect sensor performance (bandwidth, sensitivity, signal to noise ratio). The transport path 12 is shown together with the document 200. In this diagram, a non-zero sensor angle is shown although in the first aspect of the present invention this angle will be zero.

The primary parameters which impact on sensor performance are:
Sensor Distance
Transport position
Emitted, reflected, absorbed and transmitted wave
Transport Gap
Sensor angle
Burst count Sensor Distance The travel time of the acoustic burst depends on the distance between transducers 62. The burst rate is inversely proportional to the distance. A small distance will allow a greater temporal resolution.

The time between the first incoming burst and the following reflected burst is directly proportional to the distance. More time permits a better separation between needed and unneeded signals (echo).

Transport Position

The transport position between the two transducers 62 has an impact on the arrival time of the reflection that will interfere with the first burst. When the transport path 12 is in the middle of the two transducers 62, the echo can be separated more easily.

Emitted Wave

The wavelength is around 1.5 mm. The active emitting surface dimension of the transmitting transducer 62 is around 8 mm. Since it is few times greater than the wavelength, we are effectively working with planar waves. Plane waves do not have any geometrical attenuation. It means that the received energy is constant as the transducer distances increase.

Reflected Wave

Around 95% of the emitted wave is reflected by the note and or by the transducer. Reflected waves travel back and forth between the two transducers and the scanned document 200. They slowly attenuate. This ringing lasts a specific time and does not allow another measurement burst to be generated since constructive and or destructive interferences will be added to the signal. This effect decreases the signal to noise ratio of the sensor. It is avoided by the use of acoustic foam as described above.

Absorbed Wave

Acoustic absorption is related to the mass density (weight per area or volume) of the document 200. The denser the document is, the less transmitted energy will pass through the document. This property is used for tape detection.

Transport Gap

The transport gap should be as small as possible to increase the sensitivity.

Burst Count

More bursts in the emitted wave increase the received energy (more sensitivity). On the other hand the system has to deal with more reflections that can reduce the sensitivity.

Examples

Measurements have been taken in order to estimate the effectiveness of the transducer pair 62 at detecting note damage in the form of holes, knife cuts, tape and hand-made tears. The tears and cuts were "closed", i.e. they were made such that no opening was visible when observed along a line perpendicular to the note surface. The measurements were made in a note transport at a speed of 1.85 m/s. The sensor settings were the following:
  Burst count: 2
  Burst frequency: 218.75 kHz
  Burst Amplitude 20Vp-p
  RX Gain: 72 dB,
  Angle 30°
  Sensor distance: 20 mm
  Transport gap: ~2-3 mm
  Burst rate: 918 usec
  Integrator start: 66 usec
  Integration duration: 43.5 usec It will be noted that the sensor angle was set to 300 but with the previously described solution with acoustic foam clamping, the results are similar for a 0° sensor angle.

In the first set of examples, FIGS. 11-16, the effect of different types of tape adhered on different documents was examined.

Figure 11:
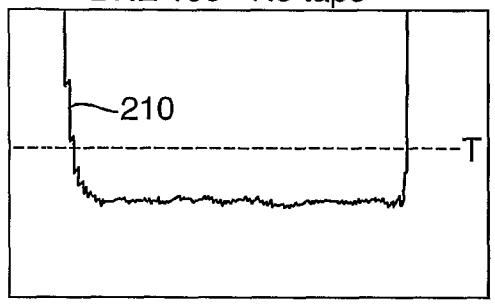
FIGS. 11-20 illustrate the amplitude of the received signal following processing obtained at a sequence of samples along various banknotes provided with tapes and holes and without any tape or hole.

FIG. 11 illustrates the output signal from a single receiving transducer following integration and sample and hold at a sequence of sample points along the length of the note in the transport direction. In this case, since there was no tape or other physical defect on the note, the received signal is substantially flat. The abbreviation "DRE" refers to a test note.

Figure 12:
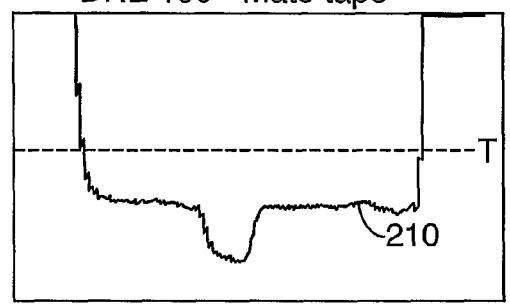

In FIG. 12, a strip of "Mate" tape was adhered across the same banknote extending perpendicular to the direction of transport. It can be seen in FIG. 12 that there is further attenuation of the ultrasound signal in the region of the tape as shown at 210.

Figure 13:
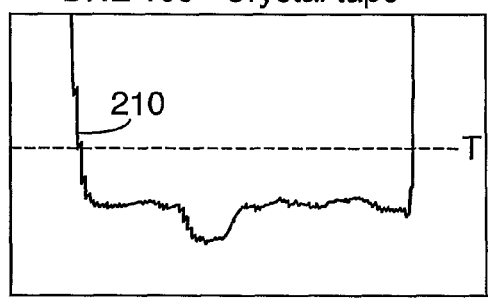

FIG. 13 is a view similar to FIG. 12 but illustrating the effect of a different type of tape, "Crystal" tape. Again, further attenuation occurs in the region of the tape although this is slightly less than in the case of the FIG. 12 example.

Figure 14:
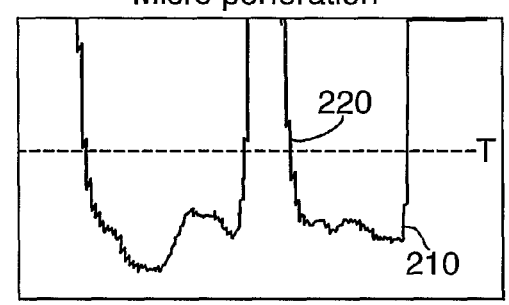

FIG. 14 illustrates the signal obtained when inspecting a CHF20 banknote provided with a tape and also a micro perforation. As in the previous examples, attenuation 210 occurs in the region of the tape while in the region of the micro perforation, there is a substantial increase in the amplitude of the received signal since there is no attenuation as shown at 220.

Figure 15:
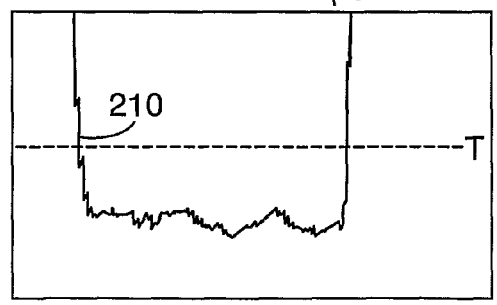
Figure 16:
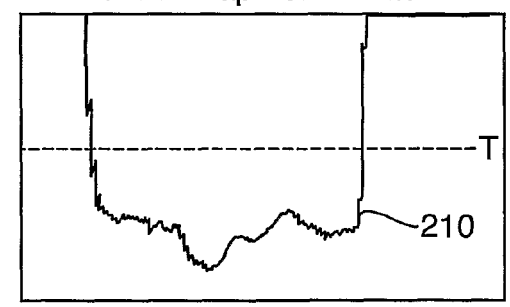

FIG. 15 illustrates the signal obtained from a five euro banknote without any tape while FIG. 16 illustrates the same note but with tape adhered on the thread of the banknote. Here a small attenuation can be seen at 210 corresponding to the tape.

Figure 17:
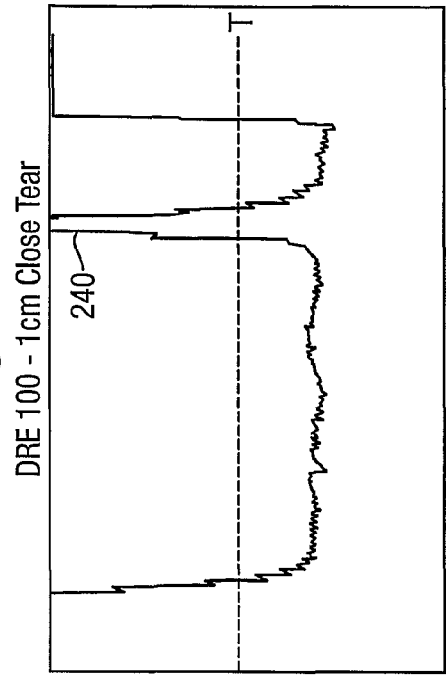

The performance of the channel has also been tested in relation to cuts, tears and holes. FIG. 17 illustrates the received signal when inspecting a DRE 100 note with a 1 cm knife cut and it can be seen that there is a significant increase in the amplitude of the received signal at 230 corresponding to the knife cut.

Figure 18:
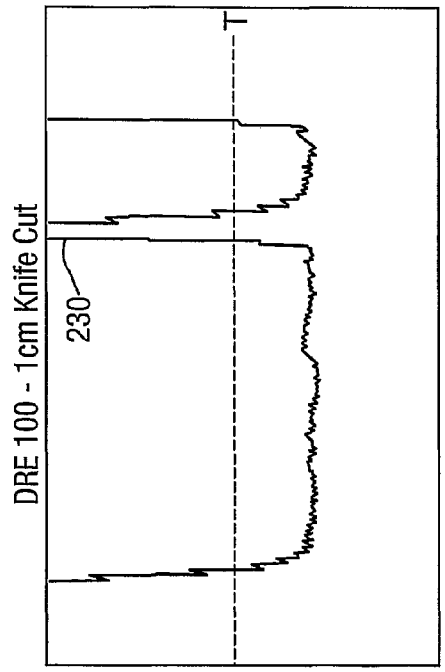

FIG. 18 illustrates the received signal when detecting a closed tear of length 1 cm as indicated at 240.

Figure 19:
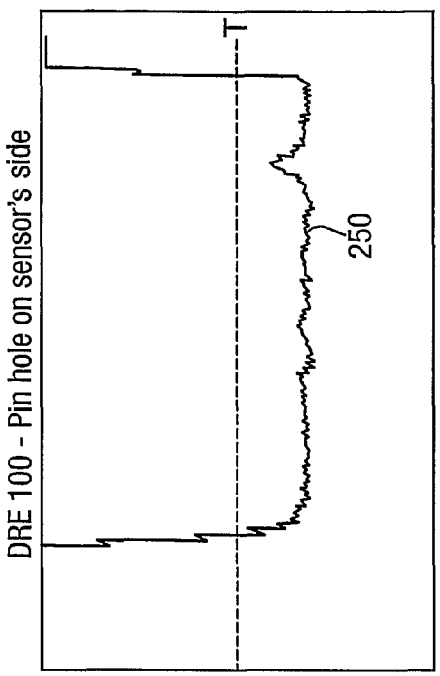

FIG. 19 illustrates the received signal when detecting a pin hole aligned with the centre of the channel, the pin hole being formed in a DRE 100 note, the signal associated with the pin hole being shown at 250.

Figure 20:
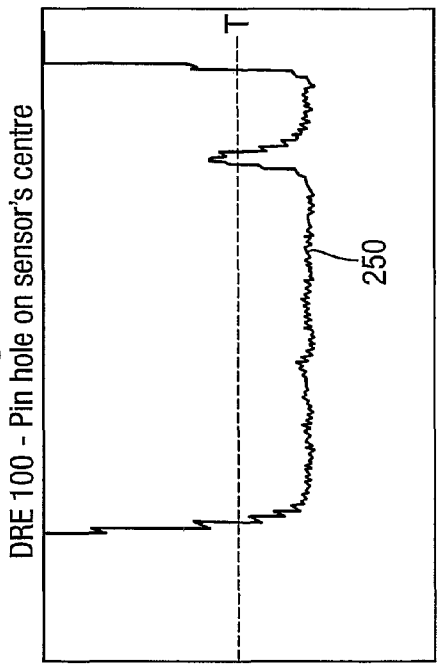
Figure 22:
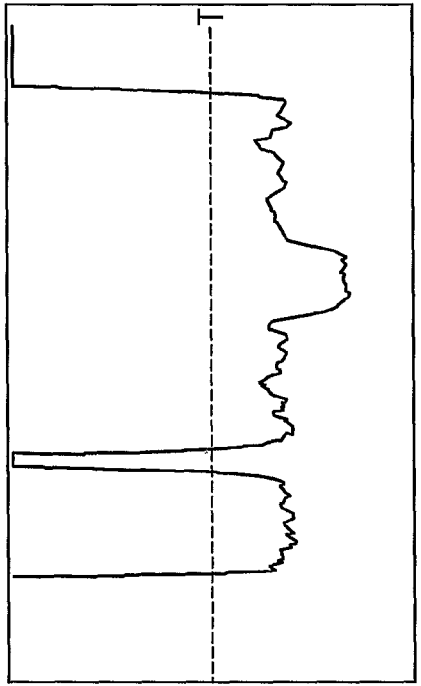
FIGS. 21-24 illustrate received signals when inspecting the same banknote but with different burst rates of 918 microseconds, 233 microseconds, 123 microseconds, and 109 microseconds respectively.
Figure 24:
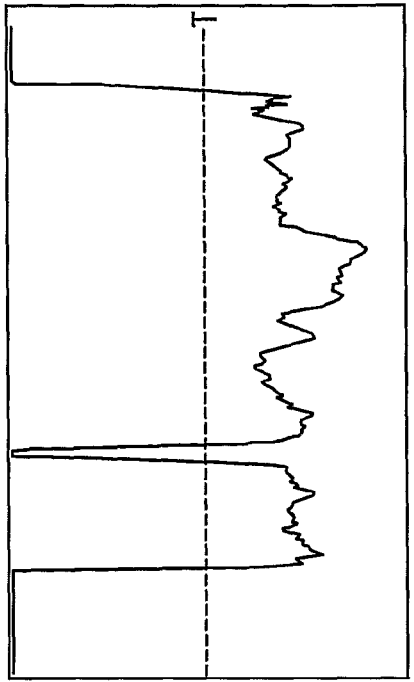
Figure 21:
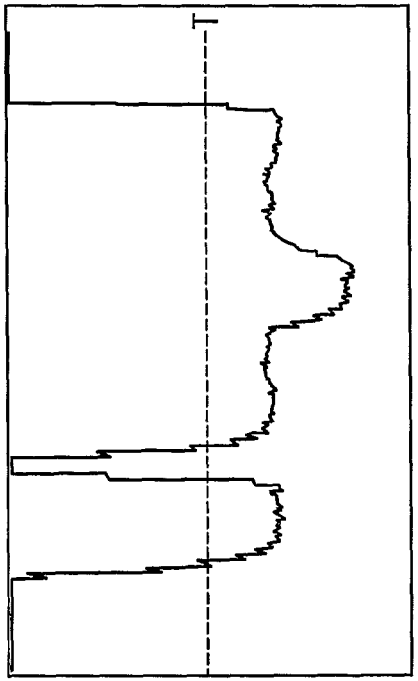
Figure 23:
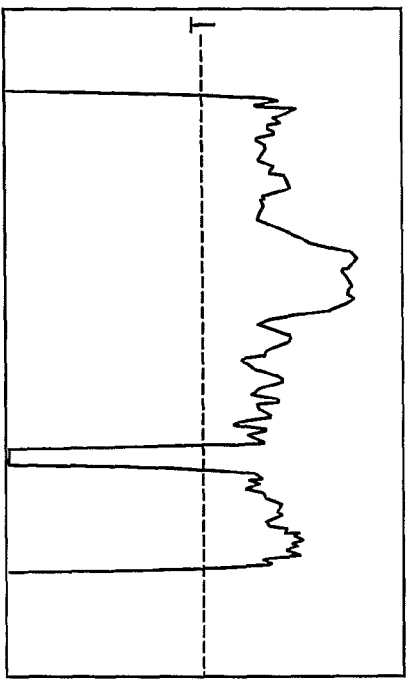
Figure 26:
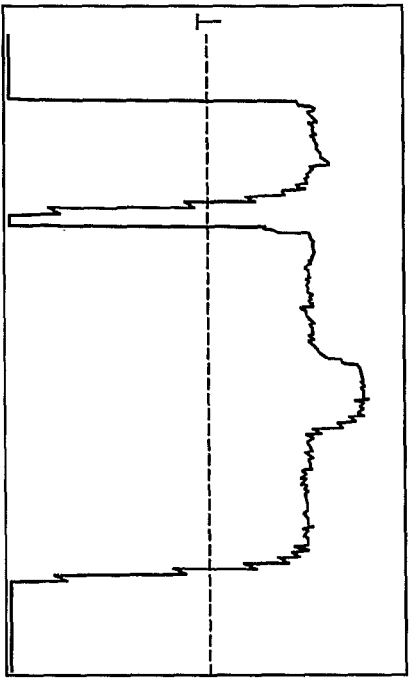
FIG. 26 is similar to FIG. 25 but with the sensor angle reduced to 0°.
Figure 28:
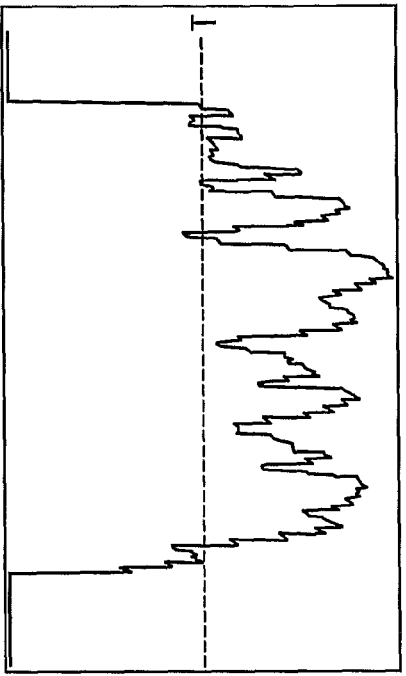
FIG. 28 is similar to FIG. 26 but with the banknote just 4 mm from one of the transmitters.
Figure 25:
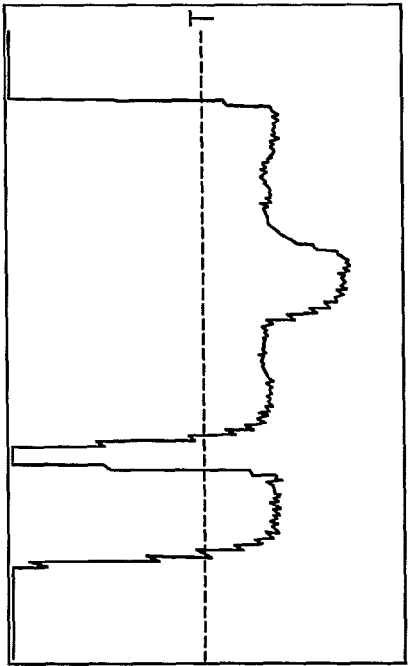
FIG. 25 illustrates the output signal from a DRE 100 banknote with a tape and closed tear with the transducers at a sensor angle of 30°, a spacing of 20 mm and with the note 10 mm from each transducer and a burst rate of 918 microseconds.
Figure 27:
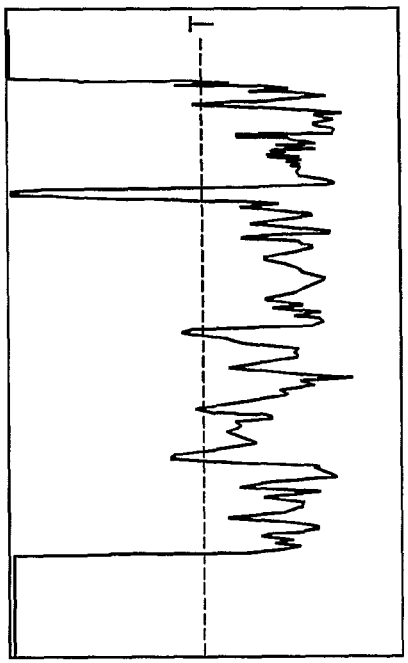
FIG. 27 is similar to FIG. 26 but with the burst rate reduced to 223 microseconds.

FIG. 20 illustrates the same situation as in FIG. 19 but with the pin hole arranged to one side of the centre of the channel.

In order to demonstrate the effect of varying burst rate on signal quality, we have undertaken a number of tests on the same document (DRE 100 with tape and closed tear) utilizing different burst rates. The results are shown in FIGS. 21-24. In each case, the transducers were arranged at a 30° sensor angle and with a distance between the transducers of 2 cm. It can be seen that for shorter burst rates there is a significant increase in noise and thus reduction in sensitivity due to the inability to exclude reflections and interference.

We have also inspected the effect of varying other parameters including sensor angle and transport position and the results are shown in FIGS. 25-28. Again, it can be seen that reducing the sensor angle (FIGS. 26 and 27) and placing the note at an offset position in relation to the spacing between the transducers significantly increases noise. However, when acoustic foam is used as in FIGS. 1-3, this problem is avoided and a zero sensor angle can be used.

Analysis of Signals

In operation, the sampled signal from each channel will be stored in a memory to produce an array of signals extending over the area of the document covered by the detector 10. The signals from each channel will be suitably processed so that the location of each sample relative to other samples is accurately determined. The second and third lines of transducers are activated line by line as the note is detected by the first row of sensors, and are turned off as the trailing edge of the note is detected passing the first row of transducers. The transducers sample the outputs at a rate decided upon by the transport system and this depends upon the speed of the note in the transport and the resolution required in order to detect tape of particular size.

The resultant, stored signals effectively generate a two-dimensional array which can then be analysed using a conventional pattern recognition or thresholding technique to identify the presence of tears, tapes, holes etc. The result of this detection can then be fed back to the sorting or other machine in which the detector is utilized so that the machine can use that information when making a decision about how to handle the banknote, for example accept or reject.

The FPGA 124,124B controls the timing of the transducer activation circuits, controls the analogue-to-digital converters and handles the bi-directional communication with the CPU 125,125B. Further, its task is to synchronize the output of the transducer arrays with the note transport speed (i.e. to delay data from the transducer array which "sees" the note earlier than the arrays later along the note path).

Figure 30:
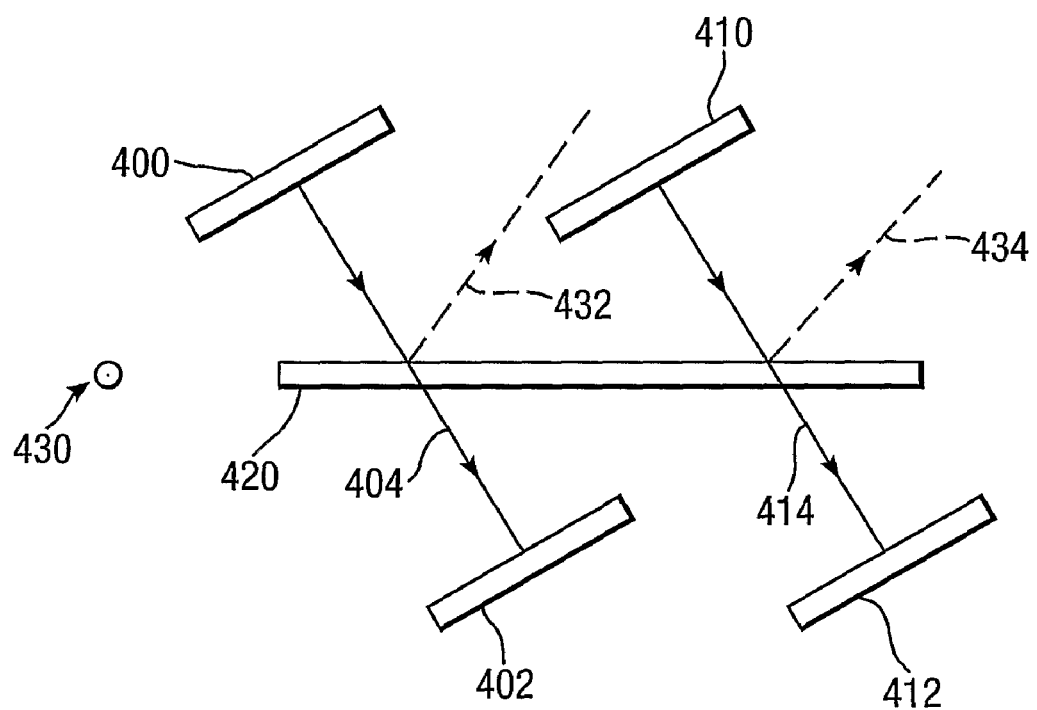
FIG. 30 is a schematic view of a second example of a system according to the invention; and, FIG. 31 illustrates schematically a system according to the invention incorporated in a document diverter system.

In the example described above, acoustic foam was used to absorb ultrasonic reflections. FIG. 30 illustrates a second embodiment in which the problem is alleviated in a different manner. In this case, two ultrasonic channels are shown comprising transmitting transducers 400,410 and corresponding receiving transducers 402,412. Respective lines of sight 404, 414 extend between the transducer pairs and traverse a document path which carries a document such as a banknote 420 in use. In this example, the transport direction is perpendicular to the diagram as indicated by arrow head 430.

The transducers are arranged such that their respective lines of sight 404,414 extend at an angle to the document path but in a plane orthogonal to the document path and the transport direction. This means that any ultrasound reflected by a document as for example indicated by lines 432,434 is reflected laterally of the transport direction and into parts of the housing (not shown) which will not reflect the ultrasound back towards the document path. In the preferred examples, the lines of sight 404,414 are located at between 30 and 45° to a normal to the document path.

Document inspection systems described above can be incorporated into a wide variety of document handling apparatus and FIG. 31 illustrates a simple example of a document sorter. As can be seen in FIG. 31, documents are supplied to the document inspection station 10 via conveyors 14,14' and are then carried by the O-rings 24A-24D, 26A-26D through the document inspection station 10 to downstream conveyors 16,16'. These conveyors pass the document to a diverter 450. The diverter 450 is controlled by a control system 460 which receives outputs from the document inspection station 10. The control system 460 determines, in the manner described above, whether a defect is present on the document such as a tape or the like and then controls the diverter 450 either to pass the document to a first location for acceptable documents or to a second location for unacceptable documents.

The invention claimed is:

1. A document inspection system comprising:
   a transport system for transporting documents along a transport path through an inspection station;
   at least one ultrasonic inspection apparatus at the inspection station, the apparatus including ultrasonic transmitting and receiving transducers arranged on opposite sides of the transport path, a processing system for monitoring ultrasonic signals received by the receiving transducer(s), and an ultrasonic absorbing material provided around the transducers and facing the transport path for absorbing ultrasound reflected by a document; and
   a document guide apparatus, including a pair of document guides on either side of the transport path, one associated with the transmitting transducer(s) and the other associated with the receiving transducer(s), each document guide including one or more rails extending parallel with the transport path, each rail having a lower coefficient of friction than the absorbing material, and extending partially over the absorbing material so as to prevent documents contacting the absorbing material in use while leaving the absorbing material exposed to the transport path at least adjacent the transducers.

2. A system according to claim 1, wherein a line of sight between the transducers extends substantially orthogonal to the transport path.

3. A system according to claim 1, wherein the one or more rails do not obstruct a line of sight between the pair of transducers.

4. A system according to claim 1, wherein the document guide apparatus is made of a metal such as aluminium.

5. A system according to claim 1, wherein the absorbing material is made of low density polyurethane foam.

6. A system according to claim 1, comprising a plurality of said ultrasound inspection apparatuses arranged in a linear array, the line extending transverse, preferably orthogonal, to the transport path.

7. A system according to claim 6, comprising more than one of said linear arrays, the arrays being arranged side by side in a direction along the transport path.

8. A system according to claim 7, wherein the transducers of one array are offset in the array direction with respect to the transducers of an adjacent array.

9. A system according to claim 1, wherein the transport system comprises at least one pair of opposed O-rings defining part of the transport path therebetween.

10. A system according to claim 1, wherein the processing system is adapted to monitor the intensity of ultrasonic signals received by the or each receiving transducer(s).

11. A system according to claim 10, wherein the processing system is adapted to compare the intensity of the received ultrasonic signals with a predetermined threshold to determine the presence of a defect, such as a hole or tear, on or in the document.

12. A system according to claim 11, wherein the processing system is adapted to provide appropriate output signals indicating the presence or absence of a defect.

13. A document inspection system comprising:
    a transport system for transporting documents along a transport path through an inspection station; and
    at least one ultrasonic inspection apparatus at the inspection station, the apparatus including ultrasonic transmitting and receiving transducers arranged on opposite sides of the transport path, and a processing system for monitoring ultrasonic signals received by the receiving transducer,
    wherein the pair of transducers define a line of sight between them which extends i) in a plane orthogonal to the transport path, and ii) at a non-orthogonal angle to the transport path within said plane, the angle being chosen so that ultrasound reflected by a document on the transport path will be reflected into a housing where it will dissipate without being received by a transducer.

14. A system according to claim 13, wherein the line of sight extends at substantially 30 degrees to the transport path.

15. A system according to claim 13, wherein the line of sight extends at substantially 45 degrees to the transport path.

16. A system according to claim 13, comprising a plurality of said ultrasound inspection apparatuses arranged in a linear array, the line extending transverse, preferably orthogonal, to the transport path.

17. A system according to claim 13, wherein the transport system comprises at least one pair of opposed O-rings defining part of the transport path therebetween.

18. A system according to claim 13, wherein the processing system is adapted to monitor the intensity of ultrasonic signals received by the receiving transducer(s).

19. A document handling apparatus comprising:
    a document inlet;
    a document outlet;
    a transport path extending between the document inlet and the document outlet; and
    a document inspection system located along a transport path, wherein the document inspection system includes:
    a transport system for transporting documents along the transport path through an inspection station;
    at least one ultrasonic inspection apparatus at the inspection station, the apparatus including ultrasonic transmitting and receiving transducers arranged on opposite sides of the transport path, a processing system for monitoring ultrasonic signals received by the receiving transducer(s), and an ultrasonic absorbing material provided around the transducers and facing the transport path for absorbing ultrasound reflected by a document; and
    a document guide apparatus, including a pair of document guides on either side of the transport path, one associated with the transmitting transducer(s) and the other associated with the receiving transducer(s), each document guide including one or more rails extending parallel with the transport path, each rail having a lower coefficient of friction than the absorbing material, and extending partially over the absorbing material so as to prevent documents contacting the absorbing material in use while leaving the absorbing material exposed to the transport path at least adjacent the transducers.

20. A document handling apparatus according to claim 19, the document handling apparatus comprising more than one document outict outlets and a diverter for guiding a document to an appropriate outlet in response to the said output signal.

21. A document handling apparatus comprising:
    a document inlet;
    a document outlet;
    a transport path extending between the document inlet and the document outlet; and
    a document inspection system located along a path, wherein the document inspection system includes:
    a transport system for transporting documents along a transport path through an inspection station; and
    at least one ultrasonic inspection apparatus at the inspection station, the apparatus including ultrasonic transmitting and receiving transducers arranged on opposite sides of the transport path, and a processing system for monitoring ultrasonic signals received by the receiving transducer(s), wherein the pair of transducers define a line of sight between them which extends i) in a plane orthogonal to the transport path, and ii) at a non-orthogonal angle to the transport path within said plane, the angle being chosen so that ultrasound reflected by a document on the transport path will be reflected into a housing where it will dissipate without being received by a transducer.

22. A document handling apparatus according to claim 21, the document handling apparatus comprising more than one document outlets and a diverter for guiding a document to an appropriate outlet in response to the said output signal.

* * * * *